(12) United States Patent
Chandler et al.

(10) Patent No.: US 12,396,933 B2
(45) Date of Patent: Aug. 26, 2025

(54) SUNSCREEN COMPOSITION

(71) Applicant: VeganicSKN Limited, Milton (AU)

(72) Inventors: Mark Chandler, Newark, DE (US);
Rainer Kröpke, Schenefeld (DE);
Fiona Wheeler, Rocklea (AU); Robert
Sasse-Jappie, Rocklea (AU)

(73) Assignee: VeganicSKN Limited, Milton (AU)

( * ) Notice: Subject to any disclaimer, the term of this patent is extended or adjusted under 35 U.S.C. 154(b) by 0 days.

(21) Appl. No.: 16/614,330

(22) PCT Filed: May 15, 2018

(86) PCT No.: PCT/AU2018/050454
§ 371 (c)(1),
(2) Date: Nov. 15, 2019

(87) PCT Pub. No.: WO2018/209382
PCT Pub. Date: Nov. 22, 2018

(65) Prior Publication Data
US 2020/0214952 A1    Jul. 9, 2020

(30) Foreign Application Priority Data
May 17, 2017  (AU) ................ 2017901839

(51) Int. Cl.
A61K 8/27 (2006.01)
A61K 8/02 (2006.01)
A61K 8/06 (2006.01)
A61Q 17/04 (2006.01)

(52) U.S. Cl.
CPC ............. A61K 8/27 (2013.01); A61K 8/0275 (2013.01); A61K 8/06 (2013.01); A61Q 17/04 (2013.01); A61K 2800/30 (2013.01); A61K 2800/34 (2013.01); A61K 2800/412 (2013.01)

(58) Field of Classification Search
None
See application file for complete search history.

(56) References Cited

U.S. PATENT DOCUMENTS

| | | |
|---|---|---|
| 7,390,355 B2 | 6/2008 | Lyth |
| 2003/0202948 A1 | 10/2003 | Koini et al. |
| 2006/0115438 A1* | 6/2006 | Vonbehren ............. A61Q 19/00 424/70.13 |
| 2006/0228310 A1 | 10/2006 | Lyth |
| 2008/0057008 A1 | 3/2008 | Naden et al. |
| 2008/0233060 A1* | 9/2008 | Grune ..................... A61K 8/63 424/59 |
| 2010/0143426 A1* | 6/2010 | Laba ........................ A61K 8/27 424/401 |
| 2010/0310871 A1 | 12/2010 | McCormick et al. |
| 2010/0316582 A1* | 12/2010 | Tsuzuki .................. A61K 8/27 424/59 |
| 2012/0107253 A1 | 5/2012 | Xing et al. |
| 2012/0263661 A1* | 10/2012 | Grune ..................... A61K 8/44 252/588 |
| 2014/0255323 A1 | 9/2014 | Ishida et al. |
| 2016/0220457 A1 | 8/2016 | Yamaguchi et al. |
| 2020/0214952 A1 | 7/2020 | Chandler et al. |

FOREIGN PATENT DOCUMENTS

| | | | |
|---|---|---|---|
| CN | 102871850 A | | 1/2013 |
| DE | 102004004969 A1 | | 8/2005 |
| JP | 2012-201660 A | | 10/2012 |
| JP | 2018-154613 A | | 10/2018 |
| KR | 20100060731 A | * | 6/2010 |
| WO | WO 93/21899 A1 | | 11/1993 |
| WO | WO2007/117352 A2 | | 10/2007 |

OTHER PUBLICATIONS

Kabana ("What is the difference between titanium dioxide and zinc oxide?", an internet article (dated Aug. 21, 2008) obtained from the website: https://kabanaskincare.com/faqs/what-is-the-difference-between-titanium-dioxide-and-zinc-oxide/) (Year: 2008).*
Antaria ("ZinClearTM The Natural Choice in Sun Care", an internet article (dated 2015) obtained from the website: https://www.deverauxspecialties.com/antaria/) (Year: 2015).*
"Sorbitan Sesquiisostearate" from EWG's Skin Deep® Cosmetics Database found at the website: EWG Skin Deep® | What is Sorbitan Sesquiisostearate (date unknown).*
English translation for KR-20100060731-A (2010).*
Chen, L.L. et al. 2013 "Nanotechnology in Photoprotection" Nanotechnology in Dermatology (Chapter 2), Eds Springer Science pp. 9-18.
International Search Report in International Application No. PCT/AU2018/050454, dated Aug. 9, 2018.

(Continued)

Primary Examiner — Sin J Lee
(74) Attorney, Agent, or Firm — Knobbe, Martens, Olson & Bear, LLP

(57) ABSTRACT

A sunscreen composition comprising from 20 to 25 wt % zinc oxide that is not surface treated and from 24 to 25 wt % water, the sunscreen composition being in the form of an emulsion having an aqueous phase and an oil phase, the sunscreen composition being free from organic UV filters or organic UV absorbers, the sunscreen composition having an SPF rating of 50 or more, the sunscreen composition being free from silicone materials and the sunscreen composition being free of titanium dioxide.

10 Claims, No Drawings

(56) References Cited

OTHER PUBLICATIONS

International Search Report in PCT/AU2019/051195, issued Dec. 19, 2019.
Database GNPD [Online] Mintel; Aug. 1, 2014 [retrieved on Dec. 16, 2019], Philosophy, USA: "Instant Skin-Tone Perfecting Moisturizer SPF 20", Database accession No. 2582521.
Database GNPD [Online] Mintel; Sep. 1, 2012 [retrieved on Dec. 2, 2019], Niuer International Skin Lab, Taiwan: "Anti-Acne Sunscreen SPF 50/PA+++", Database accession No. 1887104.
Database GNPD [Online] Mintel; Nov. 1, 2016 [retrieved on Dec. 2, 2019], Gowoonsesang Cosmetics, South Korea: "Sensi-AC Sun Cream SPF 43 PA+++", Database accession No. 4326329.
Australian Government Department of Health, Therapeutic Goods Association. Literature Review on the safety of titanium dioxide and zinc oxide nanoparticles in sunscreens [online]. Version 1.1. Canberra, ACT: TGA, 2016 [retrieved on Dec. 16, 2019]. "Chapter 2, p. 5, Nanoparticle Characteristics."

* cited by examiner

SUNSCREEN COMPOSITION

TECHNICAL FIELD

The present invention relates to a sunscreen composition.

BACKGROUND ART

As awareness increases of the risks associated with overexposure to the sun causing skin damage and skin cancer, sunscreens have become very widely used. Sunscreens are applied to the skin and desirably reflect and/or block UVA and UVB rays to prevent sunburn and skin damage. Many sunscreens include components such as organic chemical compounds that absorb UV light (such as octylmethoxy cinnamate and/or octocrylene and avobenzone), inorganic compounds that absorb or reflect UV light (such as zinc oxide or titanium dioxide) and creams or carriers that enable the sunscreen to be easily and comfortably applied to the skin.

The effectiveness of sunscreens is typically measured using an SPF (sun protection factor) rating. The SPF rating is a measure of the fraction of sunburn producing UV rays that red skin. For example, "SPF 15" means that $\frac{1}{15}^{th}$ of the burning radiation will reach the skin, assuming that the sunscreen is applied evenly at a dosage of 2 mg/cm². A user can determine the effectiveness of the sunscreen by multiplying the SPF factor by the length of time it takes for him or her to suffer sunburn without sunscreen. Therefore, if a person develops sunburn in 10 minutes without wearing a sunscreen, the same person exposed to the same intensity of sunlight will avoid sunburn for 150 minutes if wearing sunscreen with an SPF of 15. However, SPF rating is considered to be an imperfect measurement of the degree of protection provided by a sunscreen. Consequently, most countries prescribe a maximum SPF rating that can be attributed to any sunscreen. For example, in Australia, the maximum SPF rating that can be attributed to any sunscreen is SPF 50+.

Most sunscreens having an SPF rating of 50+ use organic UV filters and/or non-mineral UV filters. Mineral sunscreen products that are free from non-mineral UV filters of comparable SPF rating generally use silicone film forming ingredients. They also tend to use a mixture of zinc oxide and titanium dioxide as the mineral UV filters. They also sometimes use anti-inflammatory factors, such asbisabolol, to increase the in-vivo SPF test results of a sunscreen by delaying the reddening of the skin.

Some sunscreen products are sold as "all natural products", which typically means they are free from silicones and petrochemicals. The "all natural" sunscreen products that have SPF 50+ are generally anhydrous products (which contain no water) and are typically described as sunscreen butters or sunscreen balms. These products have a very thick consistency and some consumers resist using these products because they can be difficult to apply to the skin. This is especially so if the consumer has a significant amount of hair on the skin (such as hairy arms or hairy legs), as application of these products to hairy skin requires an extended period of rubbing or spreading to have the product evenly applied.

Sunscreen compositions that include water but exclude organic UV filters or non-mineral UV filters have difficulty in meeting testing requirements to achieve an SPF rating of 50+.

It will be clearly understood that, if a prior art publication is referred to herein, this reference does not constitute an admission that the publication forms part of the common general knowledge in the art in Australia or in any other country.

SUMMARY OF INVENTION

The present invention is directed to a sunscreen composition, which may at least partially overcome at least one of the abovementioned disadvantages or provide the consumer with a useful or commercial choice.

With the foregoing in view, the present invention in one form, resides broadly in a sunscreen composition comprising from 20 to 25% zinc oxide, and from 24 to 31% water, the sunscreen composition being in the form of an emulsion containing an aqueous phase and an oil phase, the sunscreen being free from organic UV filters or organic UV absorbers, the sunscreen having an SPF rating of 50 more.

In a second aspect, the present invention provides a sunscreen composition comprising from 20 to 25% zinc oxide, and from 24 to 31% water, the sunscreen composition including a hydrophobic phase, the sunscreen composition being in the form of an emulsion containing an aqueous phase and an organic oil phase, the sunscreen being free from organic UV filters or organic UV absorbers, the sunscreen having an SPF rating of 50 more.

Throughout this specification, all percentages of each component are given as weight percentages of the total composition.

In one embodiment, the sunscreen composition in accordance with the present invention has a zinc oxide content of from 22 to 25%, or from 23 to 25%, or from 24 to 25%, or from 24.5% to 24.999%, or from 24.5% to 24.998%, or about 24.98%, or about 25%.

In one embodiment, the sunscreen composition has water present in an amount of from 26 to 31%, or from 27 to 31%, or from 28 to 31%, or from 29 to 31%, or from 29.5 to 30.6%, or from 29.5 to 30.6%, or between 30.48 and 30.514%. In other embodiments, the water content is from 24% to 25%, or from 24% to 24.5%, or about 24.4%.

In some embodiments, the sunscreen composition of the present invention is free from silicone materials.

In one embodiment, the aqueous phase comprises water and other components that are soluble in water. The aqueous phase may include glycerin (glycerol) or other water soluble humectants, and one or more salts (such as NaCl). Other components may also be added to the aqueous phase. The components added to the aqueous phase are water soluble components.

In one embodiment, the hydrophobic phase comprises an oil phase. The oil phase may comprise one or more different compounds. Examples of compounds that may be included in the oil phase include one or more of oils, fatty acids, beeswax, phospholipids and/or glycerophospholipids, hydroxystearic acids, polyhydroxystearic acids, esters of fatty acids, polyesters of fatty acids, emulsifiers and emollients/moisturisers.

The zinc oxide that is present in the composition may be in the form of fine particles. The zinc oxide may comprise the product sold by Antaria Pty Ltd under the trade name ZinClear XP and/or Zinclear XP dispersions and/or Zinclear XP 65COCO. These products may be as described in Australian patent number 2009203996 and in international patent publication number WO 2009/089523, the entire contents of which are herein incorporated by cross-reference. The zinc oxide particles may also be the same as the zinc oxide particles used in the sunscreen composition described in Australian patent number 2003205436, the entire contents of which are herein incorporated by cross-reference.

In one embodiment, the zinc oxide comprises Zinclear XP 65COCO and ZinClear XP.

In some embodiments, the zinc oxide maybe in the form of aggregates of primary particles.

ZinClear XP comprises zinc oxide particles that are formed as aggregates of smaller particles. As described in Australian patent number 2009203996, ZinClear XP is a zinc oxide powder comprising zinc oxide agglomerates which, when used in a dispersion at a concentration of 50 weight % of zinc oxide, produces a transparent composition having a total visible transmittance through a path length of 20 µm at 550 nm of at least 70%, the powder having a number average zinc oxide aggregate size of at least 0.8 µm, wherein the aggregates are mesoporous and have a total mesopore volume of at least 0.25 cm$^3$ per gram. High-energy milling of ZinClear XP can break up the zinc oxide aggregates to reduce the overall particle size of the aggregates. ZinClear XP comprises 99 to 100% zinc oxide.

Zinclear XP 65COCO is a mixture of zinc oxide (in the form of ZinClear XP), coco-caprylate/caprate, polygylceryl-3 polyricinoleate and isostearic acid. It is a commercially available product can be purchased from Antaria Pty Ltd. Zinclear XP 65COCO is a dispersion that includes coco-caprylate/caprate as an emollient. It has high transparency and low whiteness. Zinclear XP 65COCO contains 65% zinc oxide, 30 to 31% coco-caprylate/caprate, 3.0 3.5% polygylceryl-3 polyricinoleate and 1 to 1.5% isostearic acid.

In another embodiment, the zinc oxide comprises Zin-Clear XP.

In one embodiment, the sunscreen composition of the present invention is also free of titanium dioxide.

In one embodiment, the water phase may comprise water, glycerin, sodium chloride and galactoarabinan. Glycerin and galactoarabinan are moisturisers and they may also affect the film forming capabilities of the composition.

The sunscreen of the present invention, in some embodiments, may also contain other ingredients, such as preservatives and fragrances. Chelators and other ingredients which may boost the efficiency of preservatives may also be added.

In one embodiment, the sunscreen of the present invention contains no anti-inflammatory active agents.

In a third aspect, the present invention provides a method for producing a sunscreen composition as described hereinabove, the method comprising the steps of forming an oil phase, adding zinc oxide particles to the oil phase, preparing an aqueous phase, and mixing the aqueous phase with the mixture of the zinc oxide particles and the oil phase under high shear mixing, wherein the zinc oxide particles comprise aggregates of zinc oxide and the high shear mixing breaks up the zinc oxide aggregates into smaller particles.

In one embodiment, the high shear mixing breaks up the zinc oxide aggregates into smaller particles but does not break up a significant number of the zinc oxide aggregates into primary nanoparticles. For example, less than 10% of the zinc oxide aggregates may be broken up into primary nanoparticles, or less than 5% of the zinc oxide aggregates may be broken up into primary nanoparticles, or less than 3% of the zinc oxide aggregates may be broken up into primary nanoparticles, or less than 2% of the zinc oxide aggregates may be broken up into primary nanoparticles, or less than 1% of the zinc oxide aggregates may be broken up into primary nanoparticles.

In one embodiment of the method of the present invention, the oil phase is prepared by mixing the ingredients of the oil phase and heating to an elevated temperature with uniform stirring or until all solids have completely dissolved. The oil phase may be heated to a temperature of up to 90° C., or to 80° C., or up to 75° C., or about 75° C., in this step.

The zinc oxide particles are added to the oil phase once the oil phase has been formed. The zinc oxide particles may be added under stirring and at elevated temperature.

The aqueous phase may be prepared by combining water with all the other ingredients of the aqueous phase and stirring. This step may be conducted at elevated temperature. The aqueous phase may be heated to a temperature of up to 90° C., or to 80° C., or up to 75° C., or about 75° C., in this step.

The aqueous phase may then be mixed with the mixture of zinc oxide particles and the oil phase. The combined phases may be mixed under high speed stirring. In one embodiment, the mixture of the oil phase and the zinc oxide particles are mixed under high speed stirring and the aqueous phase is added to the mixture of the zinc oxide particles in the oil phase.

Once mixed, the composition may be subjected to high shear stirring. The composition may be cool to room temperature or just above room temperature before being subjected to high shear stirring. In one embodiment, the composition is cooled to 25 to 30° C. and then subjected to high shear stirring for a period of less than 5 minutes, or for a period of less than 4 minutes, or for a period of less then 3 minutes, or for a period of less then 2 minutes, or for about 1 minute. The high shear stirring has the effect of breaking up the zinc oxide aggregates to result in a smaller particle sizes in the zinc oxide particles. Without wishing to be bound by theory, the present inventors believe that this results in a greater range of zinc oxide particle sizes in the sunscreen composition.

Initial tests conducted by the present inventors have shown that sunscreens in accordance with embodiments of the present invention tested to an SPF rating of 50 or greater. The present inventors believe that this is the first sunscreen composition that contains no organic UV filters or non-mineral UV filters that has such a high SPF rating.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

DESCRIPTION OF EMBODIMENTS

The following example has been provided to illustrate a preferred embodiment of the present invention. Therefore, it will be understood that the present invention should not be considered to be limited solely to the features as shown in the following example.

Example 1

In this example, a sunscreen containing 24.998% zinc oxide by weight was produced. The sunscreen contained no organic UV filters. The sunscreen contained no non-mineral organic filters. The sunscreen contained no silicone components. The sunscreen contained no anti-inflammatory active agents.

The zinc oxide was added to the product in two forms, being ZinClear XP 65 COCO and as the pure zinc oxide powder Zinclear XP. ZinClear XP 65 COCO comprises a dispersion of zinc oxide powder that has been formed using a high energy bead milling technique.

In this example, an oil phase was formed by mixing oil, fatty acids, waxes, emulsifiers, emollients/surfactants, and skin conditioning agents, in a mixing tank. The ingredients were gently heated to 75° C. with uniform stirring until all solids had completely dissolved. The zinc oxide particles were then mixed into the oil phase and temperature returned to 75° C. with stirring until uniform. The mixture of zinc oxide and the oil phase comprised from 67% to 68%, by weight, of the total sunscreen composition.

An aqueous phase comprising water, glycerin, sodium chloride and a polysaccharide was prepared by combining the ingredients in a container and heating to 75° C. with stirring. Water was present in an amount such that the water content of the final sunscreen composition was between 30.48 and 30.514% by weight.

The mixture of the oil phase in zinc oxide was then maintained at 75° C. and subjected to fast propeller stirring whilst the aqueous phase was gradually added at 75° C. Fast propeller stirring was maintained during addition of the aqueous phase. This stirring is not expected to affect the particle size of the zinc oxide aggregates, although testing has not yet confirmed this.

The resulting mixture was cooled to 25 to 30° C. with gentle stirring and then homogenised under high shear stirring for 1 minute to achieve the final viscosity of the emulsion. The high shear stirring resulted in the breakdown of the zinc oxide aggregates to smaller aggregates. The inventors believe that the high shear stirring will break the zinc oxide aggregates down into smaller mesoporous aggregates, but is unlikely to result in the zinc oxide aggregates being reduced to their primary particles.

The sunscreen composition was subsequently subjected to SPF testing and was found to have an SPF rating of greater than 50.

Example 2

A sunscreen composition having the following composition was prepared:

| Phase | wt % in final (%) | Ingredient | Function |
|---|---|---|---|
| A | 24.4 | Water | |
| A | 10.0 | Glycerin | Humectant |
| A | 0.3 | Mixture of phenylpropanol, propanediol, capryl glycol and tocopherol | Preservative |
| A | 0.7 | Caprylyl glycol and ethy; hexylglycerin | Preservative |
| A | 1.0 | Maltodextrin | Polymer |
| A | 0.5 | Cetyl phosphate | Emulsifier |
| A | 0.5 | Sodium cgloride | Salt |
| A | 0.1 | EDTA | Salt |
| B | 40% | Mixture of zinc oxide nanoparticles, coco-caprylate/caprate and polyglyceryl-3 polyricinoleate and isostearic acid | Active sunscreen |
| B | 7.0 | C15-C19 Alkane | Emollient |
| B | 5.5 | *Jojoba* seed oil | Emollient |
| B | 5.0 | Polyglycerul - 3 polyricioleate | Emollient |
| B | 4.0 | Yellow Beeswax | Wax |
| B | 1.0 | Polyhydroxystearic acid | Dispersant |

Zinc oxide was present in an amount of 25% by weight in the final product.

The product was made by mixing and heating the ingredients of phase A to 75° C., sequentially mixing and heating the ingredients of phase B to 75° C., maintaining he on both faces and stirring until uniform, adding phase B to phase A slowly with propeller stirring, and homogenising until glossy, if needed. The product had an SPF rating of greater than 50

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. A sunscreen composition comprising from 20 to 25 wt % zinc oxide that is not surface-treated and from 24 to 25 wt % water, the sunscreen composition being in the form of an emulsion having an aqueous phase and an oil phase, the sunscreen composition being free from organic UV filters or organic UV absorbers, the sunscreen composition having an SPF rating of 50 or more, the sunscreen composition being free from silicone materials and the sunscreen composition being free of titanium dioxide;
wherein the oil phase is a hydrophobic phase consisting of:
the zinc oxide; and
one or more components selected from the group consisting of: oils, fatty acids, beeswax, phospholipids and/or glycerophospholipids, hydroxystearic acids, polyhydroxystearic acids, esters of fatty acids, polyesters of fatty acids, emulsifiers and emollients/moisturizers.

2. A sunscreen composition as claimed in claim 1, wherein the sunscreen composition has a zinc oxide content of from 22 to 25 wt %.

3. A sunscreen composition as claimed in claim 1, wherein the sunscreen composition has a zinc oxide content of from 24 to 25 wt %.

4. A sunscreen composition as claimed in claim 1, wherein the sunscreen composition has a zinc oxide content of from 24.5 wt % to 24.999 wt %.

5. A sunscreen composition as claimed in claim 1, wherein the sunscreen composition has a zinc oxide content of 24.98 wt % or 25.0 wt %.

6. A sunscreen as claimed in claim 1 wherein the sunscreen composition has water present in an amount of from 24 wt % to 24.5 wt %.

7. A sunscreen composition as claimed in claim 1, wherein the aqueous phase comprises water and one or more components that are soluble in water selected from the group consisting of glycerin (glycerol), water soluble humectants, and salts.

8. A sunscreen composition as claimed in claim 1, wherein the zinc oxide is in the form of aggregates of primary particles.

9. A sunscreen composition as claimed in claim 1, wherein the zinc oxide is present in the form of aggregates of zinc oxide particles, having an average zinc oxide aggregate size of at least 0.8 µm, wherein the aggregates are mesoporous and have a total mesopore volume of at least 0.25 $cm^3$ per gram; wherein when the zinc oxide is used at a concentration of 50 weight % in a dispersion, it produces a transparent composition having a total visible transmittance through a path length of 20 µm at a wavelength of 550 nm of at least 70%.

10. A sunscreen composition as claimed in claim 1, wherein the sunscreen composition contains no anti-inflammatory active agents.

* * * * *